United States Patent [19]
Dimitriu

[11] Patent Number: 5,968,055
[45] Date of Patent: Oct. 19, 1999

[54] AMNIOTIC MEMBRANE PERFORATOR

[75] Inventor: Dan G. Dimitriu, San Antonio, Tex.

[73] Assignee: Prism Enterprises, Inc., San Antonio, Tex.

[21] Appl. No.: 09/076,176

[22] Filed: May 11, 1998

[51] Int. Cl.$^6$ ................................................ A61B 17/42
[52] U.S. Cl. ......................... 606/125; 606/185; 606/167; 606/1; 606/171; 606/184
[58] Field of Search .................... 606/125, 167, 606/185, 184, 171, 1; 604/176, 115; 30/298, 286; 401/8

[56] References Cited

U.S. PATENT DOCUMENTS

| | | | |
|---|---|---|---|
| D. 32,846 | 6/1900 | Casselman . | |
| 1,135,987 | 4/1915 | Beecher . | |
| 1,663,761 | 3/1928 | Johnson . | |
| 2,616,434 | 11/1952 | Cataldo | 30/298 |
| 2,635,444 | 4/1953 | Carlson | 606/125 |
| 2,676,595 | 4/1954 | Dyekjaer | 128/305 |
| 2,811,969 | 11/1957 | Shubert | 606/125 |
| 3,624,747 | 11/1971 | McKnight et al. | 128/361 |
| 3,670,733 | 6/1972 | Carlisle | 128/305 |
| 5,087,262 | 2/1992 | Sheahon | 606/125 |
| 5,412,871 | 5/1995 | Reyburn et al. | 30/2 |
| 5,539,983 | 7/1996 | Reyburn et al. | 30/2 |
| 5,569,283 | 10/1996 | Green et al. | 606/170 |

OTHER PUBLICATIONS

Galenica Inc., Amniotic Membrane Perforator (copy of packaging and photograph of sample).
Hollister Amnihook™ Amniotic Membrane Perforator (photograph of sample).
Surgi–Hook (photograph of sample).

*Primary Examiner*—Michael Buiz
*Assistant Examiner*—(Jackie) Tan-uyen T. Ho
*Attorney, Agent, or Firm*—Leydig, Voit & Mayer, Ltd.

[57] ABSTRACT

An amniotic membrane perforator comprising an elongated shaft portion having an arcuate bend at the proximal end of the shaft and a hook at the distal end of the shaft. A flag portion extends perpendicularly to the shaft substantially adjacent the distal end of the shaft, opposite the hook. The cross-section of an extended length of the shaft inward the distal end is substanially oval. During use, the physician's index finger is placed along the flat portion, and the thumb and second finger adjacent the oval cross-section portion.

20 Claims, 3 Drawing Sheets

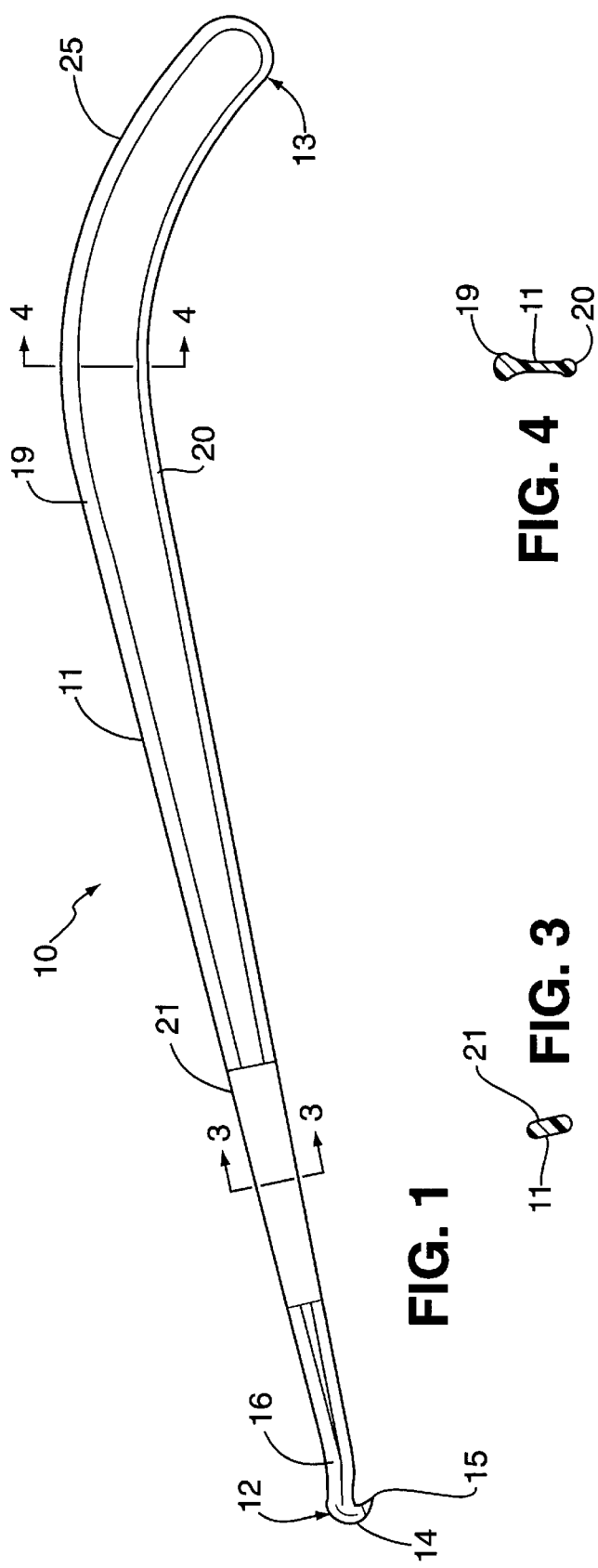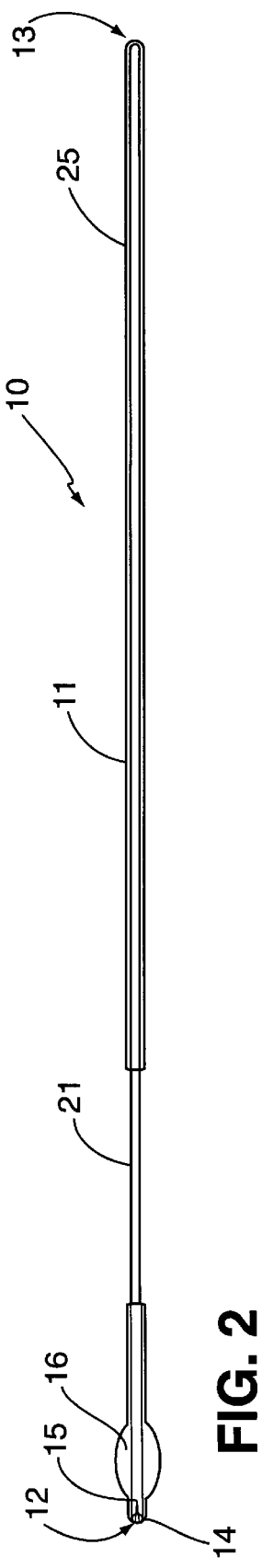

AMNIOTIC MEMBRANE PERFORATOR

TECHNICAL FIELD OF THE INVENTION

The present invention relates to medical devices, and more particularly relates to an amniotic membrane perforator for rupturing the amniotic sac during labor.

BACKGROUND OF THE INVENTION

During the labor stage of childbirth, it is sometimes necessary to enhance or accelerate the birthing process. Rupturing the amniotic sac or "bag of water" to allow the amniotic fluid to escape from the sac typically enhances uterine contractions. In rupturing the sac, hook type instruments are generally used by the physician to hook and pierce a part of the amniotic sac.

Amniotic hook instruments are typically flat, elongated stick-like structures having a sharp hook at the distal end thereof. These instruments can be cumbersome and difficult to maintain in a stable position and maneuver within the birth canal and womb.

An alternate amniotic membrane perforator design is disclosed in U.S. Pat. No. 5,087,262 to Sheahon. The '262 patent discloses a similarly structured, flat, stick-like device with a sharp prong extending axially from the distal end of the stick. As with most hook-type instruments, the device disclosed in the '262 patent is likewise difficult to maintain in a stable position and maneuver.

OBJECTS OF THE INVENTION

It is a primary object of the present invention to provide an amniotic membrane perforator that is easy to maintain in a stable position and maneuver within the birthing canal and womb. A related object of the invention to provide the physician enhanced control of the distal end of the perforator during use.

An additional object of the invention is to provide a perforator that is ergonomically friendly to the physician's hand and conforms to the bend of the physician's wrist.

These and other objects of the invention will become apparent upon review of the following description of the invention.

BRIEF SUMMARY OF THE INVENTION

The present invention provides an amniotic membrane perforator having a structure that is particularly adapted for strength, as well as the physician's comfort and control. The perforator includes an elongated shaft portion having a rounded distal end with a sharp hook portion. The elongated shaft has a generally rounded "I-beam" like shape, providing the perforator with strength and resistance to bending along the length of the shaft. To prevent the movement of the physician's wrist from interfering with the manipulation of the perforator, the shaft is provided with an arch substantially adjacent the proximal end thereof. When the physician cradles the perforator in his/her hand, the arch is disposed subjacent the inside bend of the physician's wrist so that the physician is afforded a full range of wrist motion during use.

The distal end of the perforator is likewise provided with features that enhance the physician's use thereof. The perforator includes an enlarged flat portion extending normal to the elongated shaft substantially adjacent or just inward the distal end of the perforator. The flat is opposite the hook, such that the physician may place his/her index finger on the flat to precisely guide the hook, and facilitate the precise application of pressure to the hook during use.

Additionally, spaced inward the enlarged flat portion, the cross-section of the shaft is oval for approximately one and one-half inches, rather than of the "I-beam" type cross-section. This presents a smooth gripping surface for the physician's thumb and second finger, providing added comfort to the user.

Thus, the inventive perforator provides a device that is comfortable for the physician to cradle in the hand and adjacent the wrist. Additionally, the device provides enhanced maneuverability during use in that the physician can readily control the level of force applied to the hook.

BRIEF DESCRIPTION OF THE DRAWINGS

FIG. 1 is a side elevational view of an amniotic membrane perforator constructed in accordance with teachings of the present invention.

FIG. 2 is a bottom view of the amniotic membrane perforator of FIG. 1.

FIG. 3 is a cross-sectional view taken along line 3—3 in FIG. 1.

FIG. 4 is a cross-sectional view taken along line 4—4 in FIG. 1.

Figure 7:
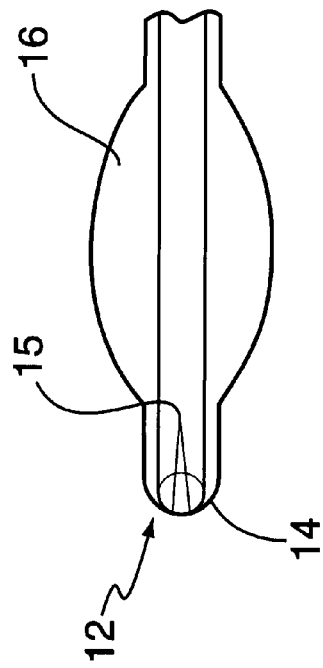
FIG. 7 is an enlarged fragmentary bottom view of the distal end of the amniotic membrane perforator of FIG. 1.
Figure 6:
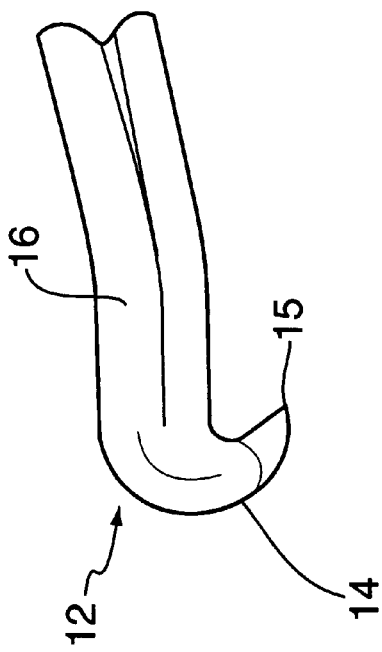
FIG. 6 is an enlarged fragmentary side view of the distal end of the amniotic membrane perforator of FIG. 1.

While the invention will be described in connection with a preferred embodiment, there is no intent to limit it to that embodiment. On the contrary, the intent is to cover all alternatives, modifications, and equivalents included within the spirit and scope of the invention as defined by the appended claims.

DETAILED DESCRIPTION OF THE INVENTION

Turning now to the drawings, there is shown an amniotic membrane perforator 10 constructed in accordance with teachings of the invention. The perforator 10 includes an elongated, widened shaft 11 having a distal end 12 and a proximal end 13. The distal end 12 has a rounded structure 14, and is provided with a sharp, pointed hook 15 along the bottom of the perforator 10.

Figure 5:
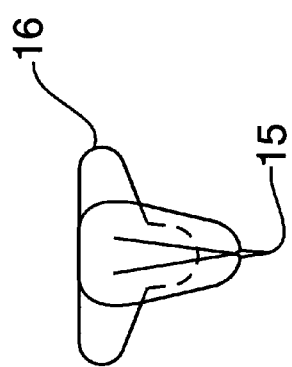
FIG. 5 is an enlarged end view of the distal end of the amniotic membrane perforator of FIG. 1.
Figure 8:
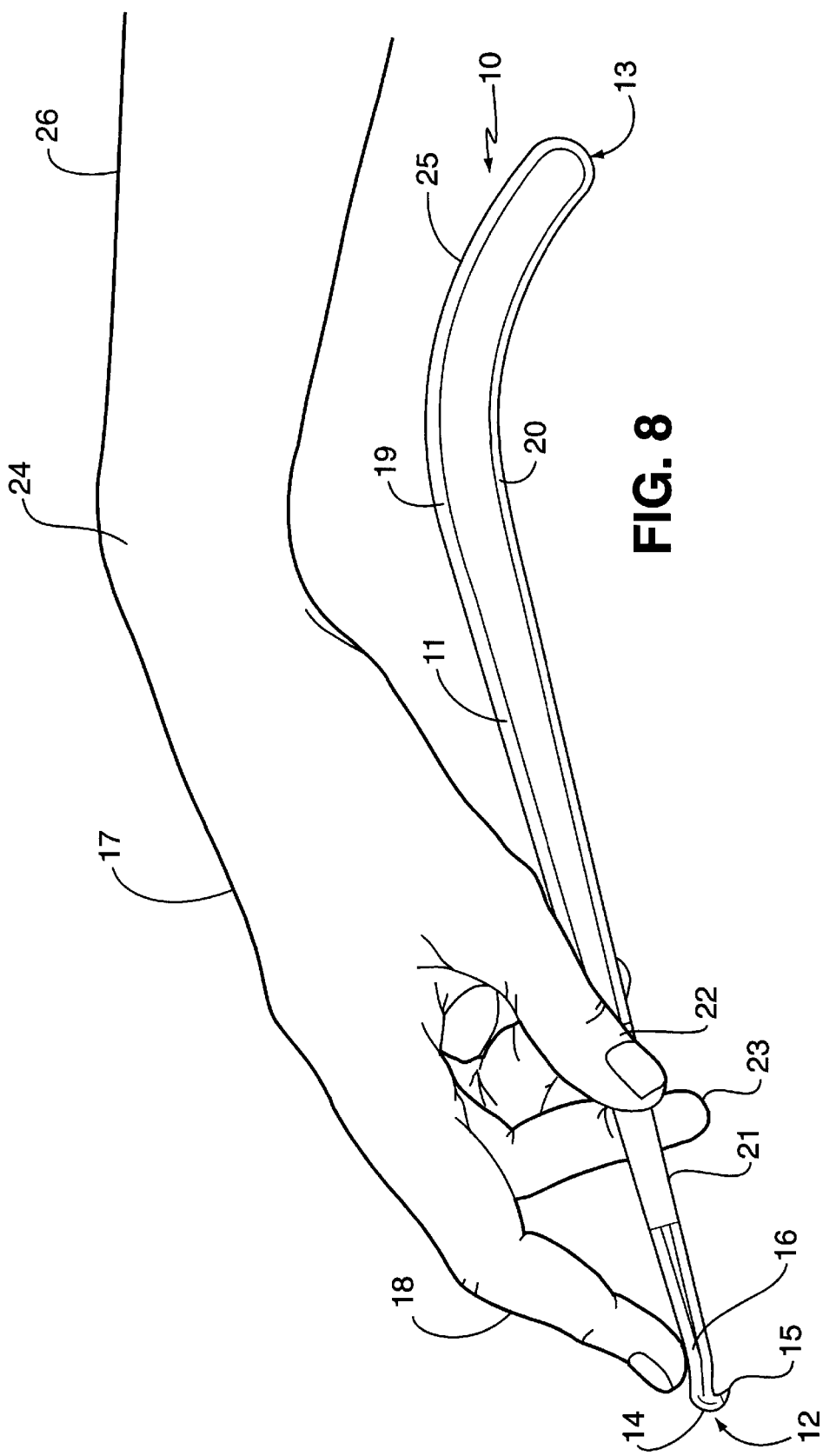
FIG. 8 is a side view of the amniotic membrane perforator of FIG. 1 cradled in the hand of a user.

In accordance with the invention, the perforator 10 is particularly adapted to provide the physician enhanced control and comfort during use. In order to provide the physician added leverage when applying a force to the hook 15 of the perforator 10, a widened flat portion 16 is provided near or adjacent the distal end 12 (see FIGS. 2, 5, and 7). The flat portion 16 is disposed along the upper edge of the shaft 11, opposite the pointed hook 15, and preferably has an elongated disk shape such that it does not present any sharp edges along its side surfaces. As shown in FIG. 8, when the perforator 10 is cradled within the physician's hand 17, the index finger 18 is disposed along the widened flat portion 16.

To provide the perforator with strength and resistance to side to side bending, the shaft 11 has a modified "I-beam" type cross-section having rounded beads 19, 20 along the upper and lower edges of the shaft 11, as shown in FIG. 4. Thus, it presents only smooth edges to the physician as well as the patient along the length of the shaft 11. It will be appreciated by those skilled in the art that this structure provides inherent mechanical benefits with regard to strength, while minimizing the quantity of material required.

In order to provide the physician added comfort during use, a length 21 of the shaft 11 which is disposed adjacent the physician's thumb 22 and second finger 23 during use does not include this "I-beam" type cross-section. Rather, the cross-section over this length 21 is oval, as shown in FIG. 3. Thus, the shaft 11 over this length 21 presents a smooth, substantialy flat contact surface to the physician's thumb 22 and finger 23, as shown in FIG. 8.

It will be appreciated by those skilled in the art that during use, the physician may bend and twist his/her wrist 24 when maneuvering the perforator 11 to pierce the amniotic sac. Accordingly, in perforators having straight elongated shafts, the proximal end of the perforator often contacts and engages the inner surface of the physician's forearm, which may interfere with movement of the hand. In order to minimize or eliminate this interference with the manipulation of the perforator presented by the perforator's contact with the physician's forearm, the inventive perforator 10 comprises a bent or an arched portion 25 substantially adjacent the proximal end 13 of the shaft 11. As illustrated in FIG. 8, the arched portion 25 arches toward the hook 15 such that when the perforator 10 is cradled in the physician's hand, the arched portion 25 is disposed subjacent the physician's wrist 24 and forearm 26 so as to not interfere with bending of the wrist 24.

The amniotic membrane perforator 10 is preferably integrally molded of a polymeric material. The perforator may be formed of conventional molding techniques, such as injection molding.

In summary, the invention provides an amniotic membrane perforator 10 that provides the physician with added comfort as well as maneuverability. Accordingly, the perforator 10 overcomes many of the shortcomings inherent in the prior art.

While this invention has been described with emphasis upon preferred embodiments, it will be obvious to those of ordinary skill in the art that the preferred embodiments may be varied. Accordingly, this invention includes all modifications encompassed within the spirit and scope of the appended claims.

What is claimed is:

1. An amniotic membrane perforator to be cradled in the hand of a user, the perforator comprising:
   an elongated shaft having a proximal end and a distal end, the shaft being substantially disposed in a first plane;
   a hook disposed at the distal end of the shaft;
   a widened flat portion disposed in a second plane substantially normal to the first plane, the flat portion being disposed substantially at or adjacent the distal end of the shaft and opposite the hook such that when the perforator is cradled in the user's hand, an index finger of the user may be disposed adjacent the flat portion whereby the user may control the movement of the hook in the first plane by the index finger exerting a force on the widened flat portion.

2. The amniotic membrane perforator of claim 1 wherein the shaft further comprises an arcuate portion substantially adjacent the proximal end.

3. The amniotic membrane perforator of claim 1 wherein the shaft has an I-beam-like cross-section along at least a portion of its length.

4. The amniotic membrane perforator of claim 1 wherein the shaft has a oval cross-section along a portion of its length spaced inward from the distal end of the shaft.

5. The amniotic membrane perforator of claim 3 wherein the shaft has a oval cross-section along a portion of its length spaced inward from the distal end of the shaft.

6. The amniotic membrane perforator of claim 2 wherein the shaft has an I-beam-like cross-section along at least a portion of its length.

7. The amniotic membrane perforator of claim 2 wherein the shaft has a oval cross-section along a portion of its length spaced inward from the distal end of the shaft.

8. The amniotic membrane perforator of claim 6 wherein the shaft has a oval cross-section along a portion of its length spaced inward from the distal end of the shaft.

9. The amniotic membrane perforator of claim 1 wherein the flat portion is oval shaped.

10. The amniotic membrane perforator of claim 9 wherein the flat portion is on the order of one-quarter of an inch wide.

11. An amniotic membrane perforator to be cradled in the hand of a user, the perforator comprising:
    an elongated shaft having a proximal end and a distal end, the shaft being substantially disposed in a first plane;
    a hook disposed at the distal end of the shaft;
    the shaft further comprises an arcuate portion substantially adjacent the proximal end, the arcuate portion being adapted to be disposed substantially subjacent the user's wrist when cradled in the user's hand.

12. The amniotic membrane perforator of claim 11 further comprising a widened flat portion disposed in a second plane substantially normal to the first plane, the flat portion being disposed substantially at or adjacent the distal end of the shaft and opposite the hook such that when the perforator is cradled in the user's hand, an index finger of the user may be disposed adjacent the flat portion.

13. The amniotic membrane perforator of claim 11 wherein the shaft has an I-beam-like cross-section along at least a portion of its length.

14. The amniotic membrane perforator of claim 11 wherein the shaft has a oval cross-section along a portion of its length spaced inward from the distal end of the shaft.

15. The amniotic membrane perforator of claim 13 wherein the shaft has a oval cross-section along a portion of its length spaced inward from the distal end of the shaft.

16. The amniotic membrane perforator of claim 11 wherein the arcuate portion has a radius on the order of 2¹⁄₂₄ inches.

17. The amniotic membrane perforator of claim 11 wherein the arcuate portion has a radius shaft on the order of 2 to 3 inches.

18. The amniotic membrane perforator of claim 16 wherein the arcuate portion has an arc on the order of 45° to 60°.

19. The amniotic membrane perforator of claim 11 wherein the flat portion is oval shaped.

20. The amniotic membrane perforator of claim 19 wherein the flat portion is on the order of one-quarter of an inch wide.

* * * * *

UNITED STATES PATENT AND TRADEMARK OFFICE
CERTIFICATE OF CORRECTION

PATENT NO.   : 5,968,055
DATED        : October 19, 1999
INVENTOR(S)  : Dan G. Dimitriu It is certified that errors appear in the above-identified patent and that said Letters Patent is hereby corrected as shown below:

In Column 2, line 64: "cross-section having" should read "cross-section, having".

In the Claims:

In Claim 16, Column 4, Line 49: "2 1/24" should read "2 ½".

Signed and Sealed this

Twenty-second Day of August, 2000

Attest:

Q. TODD DICKINSON

*Attesting Officer*          *Director of Patents and Trademarks*